US00PP21990P2

(12) United States Plant Patent
Stephens

(10) Patent No.: US PP21,990 P2
(45) Date of Patent: Jun. 28, 2011

(54) ***ALBIZIA* PLANT NAMED 'NURCAR 10'**

(50) Latin Name: *Albizia julibrissin*
Varietal Denomination: Nurcar 10

(76) Inventor: Carroll Theodore Stephens, North Augusta, SC (US)

( * ) Notice: Subject to any disclaimer, the term of this patent is extended or adjusted under 35 U.S.C. 154(b) by 0 days.

(21) Appl. No.: 12/584,121

(22) Filed: Aug. 31, 2009

(51) Int. Cl.
*A01H 5/00* (2006.01)

(52) U.S. Cl. ..... Plt./216

(58) Field of Classification Search ..... Plt./216
See application file for complete search history.

*Primary Examiner* — June Hwu
(74) *Attorney, Agent, or Firm* — C. A. Whealy

(57) ABSTRACT

A new and distinct cultivar of *Albizia* plant named 'Nurcar 10', characterized by its upright plant habit with outwardly arching lateral branches; vigorous growth habit; developing foliage greyed green in color becoming dark greyed purple with development; dark foliage color is retained during the summer and autumn; and good garden performance.

3 Drawing Sheets

Botanical designation: *Albizia julibrissin.*
Cultivar denomination: 'NURCAR 10'.

BACKGROUND OF THE INVENTION

The present invention relates to a new and distinct cultivar of *Albizia* plant, botanically known as *Albizia julibrissin* and hereinafter referred to by the name 'Nurcar 10'.

The new *Albizia* plant is a product of a planned breeding program conducted by the Inventor in North Augusta, S.C. The objective of the breeding program is to develop new *Albizia* plants with dark-colored foliage that is maintained during the summer and autumn.

The new *Albizia* plant originated from a self-pollination conducted by the Inventor in June, 2003 of *Albizia julibrissin* 'Red Leaf', not patented. The new *Albizia* plant was discovered and selected by the Inventor as a single plant within the progeny of the stated self-pollination in a controlled environment in North Augusta, S.C. in November, 2003.

Asexual reproduction of the new *Albizia* plant by chip-budding in an outdoor nursery in Belvedere, Tenn. since January, 2006, has shown that the unique features of this new *Albizia* plant are stable and reproduced true to type in successive generations of asexual reproduction.

SUMMARY OF THE INVENTION

Plants of the new *Albizia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Nurcar 10'. These characteristics in combination distinguish 'Nurcar 10' as a new and distinct cultivar of *Albizia:*

1. Upright plant habit with outwardly arching lateral branches.
2. Vigorous growth habit.
3. Developing foliage is greyed green in color becoming dark greyed purple with development.

4. Dark foliage color is retained during the summer and autumn.
5. Good garden performance.

Plants of the new *Albizia* can be compared to plants of the parent, 'Red Leaf'. Plants of the new *Albizia* differ from plants of 'Red Leaf' in the following characteristics:

1. Leaflets of plants of the new *Albizia* develop their dark greyed purple color earlier than plants of 'Red Leaf'.
2. Fully expanded leaflets of the new *Albizia* are slightly darker in color than fully expanded leaflets of 'Red Leaf'.
3. Dark leaflet color of plants of the new *Albizia* is retained during the summer and autumn whereas leaflet color of plants of 'Red Leaf' fades during the summer and autumn.

Plants of the new *Albizia* can be compared to plants of the *Albizia julibrissin* 'Summer Chocolate', disclosed in U.S. Plant Pat. No. 13,822. Plants of the new *Albizia* differ from plants of 'Summer Chocolate' in the following characteristics:

1. Leaflets of plants of the new *Albizia* develop their dark greyed purple color earlier than plants of 'Summer Chocolate'.
2. Fully expanded leaflets of the new *Albizia* are slightly darker in color than fully expanded leaflets of 'Summer Chocolate'.
3. Dark leaflet color of plants of the new *Albizia* is retained during the summer and autumn whereas leaflet color of plants of 'Summer Chocolate' fades during the summer and autumn.

BRIEF DESCRIPTION OF THE PHOTOGRAPHS

The accompanying colored photographs illustrate the overall appearance of the new *Albizia* plant, showing the colors as true as it is reasonably possible to obtain in colored reproductions of this type. Colors in the photographs may differ slightly from the color values cited in the detailed botanical description which accurately describe the colors of the new *Albizia* plant. The photographs were taken during the late summer and plants were grown under similar conditions as the plants used for the description.

The photograph on the first sheet is a side perspective view of a typical one-year old plant of 'Nurcar 10' grown in a three-quart container.

The photograph on the second sheet is a comparative close-up view of a typical lateral branch of 'Nurcar 10' (top) and a typical lateral branch of 'Summer Chocolate' (bottom).

The photograph on the third sheet is a close-up view of typical inflorescences of 'Nurcar 10'.

DETAILED BOTANICAL DESCRIPTION

The following observations, measurements and values describe plants of the new *Albizia* grown in 5-gallon containers in Aiken County, S.C. during the late summer in an outdoor nursery and under conditions which closely approximate commercial production. During the production of the plants, day temperatures ranged from 31° C. to 41° C. and night temperatures ranged from 20° C. to 24° C. Plants were two years old when the description was taken. In the description, color references are made to The Royal Horticultural Society Colour Chart, 2001 Edition, except where general terms of ordinary dictionary significance are used.

Botanical classification: *Albizia julibrissin* 'Nurcar 10'.

Parentage:

*Female, or seed, parent.*—*Albizia julibrissin* 'Red Leaf', not patented.

*Male, or pollen, parent.*—*Albizia julibrissin* 'Red Leaf', not patented.

Propagation:

*Type.*—By tissue culture.

*Root description.*—Fibrous; finely-branched; color, close to 157C.

Plant description:

*Plant form and growth habit.*—Tree; upright plant habit with outwardly arching lateral branches forming spreading crowns; vigorous growth habit.

*Plant height.*—About 2.5 meters.

*Plant diameter* (*area of spread*).—About 1.5 meters.

Lateral branch description:

*Length.*—About 30 cm to 100 cm.

*Diameter.*—About 5 mm to 10 mm.

*Internode length.*—About 30 cm.

*Angle.*—About 35° to 65° from vertical.

*Strength.*—Strong.

*Texture.*—Smooth, glabrous.

*Color.*—Close to 197B to 197C.

Foliage description:

*Arrangement.*—Alternate; bipinnately compound; leaflets sessile.

*Leaflet length.*—About 7 mm to 10 mm.

*Leaflet width.*—About 2 mm to 4 mm.

*Leaflet shape.*—Obliquely lanceolate.

*Leaflet apex.*—Acuminate.

*Leaflet base.*—Oblique.

*Leaflet margin.*—Entire; ciliate.

*Leaflet texture, upper and lower surfaces.*—Puberulent.

*Venation pattern.*—Obliquely pinnate.

*Color.*—Developing leaves, upper and lower surfaces: Close to 189A. Fully expanded leaves, upper surface: Close to 187A; venation, close to 187A. Fully expanded leaves, lower surface: Close to 59A; venation, close to 59A.

Flower description:

*Flower appearance/arrangement.*—Single apetalous flowers arranged in terminal corymbose racemes; typically about six to twelve flowers per raceme.

*Natural flowering season.*—Flowering typically occurs during the early summer in South Carolina.

*Flower longevity.*—Individual flowers last about two to three days on the plant; flowers not persistent.

*Fragrance.*—Soft, sweet.

*Inflorescence height.*—About 7 cm to 10 cm.

*Inflorescence diameter.*—About 7 cm to 8 cm.

*Flower length.*—About 3.5 cm.

*Flower diameter.*—About 3.5 cm.

*Flower bud.*—Length: About 1.5 cm. Diameter: About 2 mm to 3 mm. Shape: Narrowly elongate. Color: Close to 188B.

*Peduncles.*—Length: About 7 mm to 10 mm. Diameter: About 1 mm. Texture: Smooth, glabrous. Color: Close to 178A.

*Reproductive organs.*—Androecium: Quantity per flower: Numerous, about 80 to 230. Filament length: About 3.5 cm to 4 cm. Filament color: Close to 63A. Anther shape: Oval. Anther, length: About 0.1 mm. Anther color: Close to 153B. Amount of pollen: Scarce. Pollen color: Close to 153D. Gynoecium: Quantity per flower: Numerous, about 40 to 120. Pistil length: About 3.5 cm. Style length: About 2 cm to 3 cm. Style color: Close to 63A. Stigma shape: Rounded. Stigma color: Close to 63A. Ovary color: Close to 157A.

*Seeds/fruits.*—Seed and fruit development have not been observed.

Garden performance: Plants of the new *Albizia* have been observed to have good garden performance and to tolerate rain, wind and temperatures ranging from about −20° C. to about 41° C.

Pathogen/pest resistance: Plants of the new *Albizia* have not been observed to be resistant to pathogens and pests common to *Albizia*.

It is claimed:

1. A new and distinct *Albizia* plant named 'Nurcar 10' as illustrated and described.

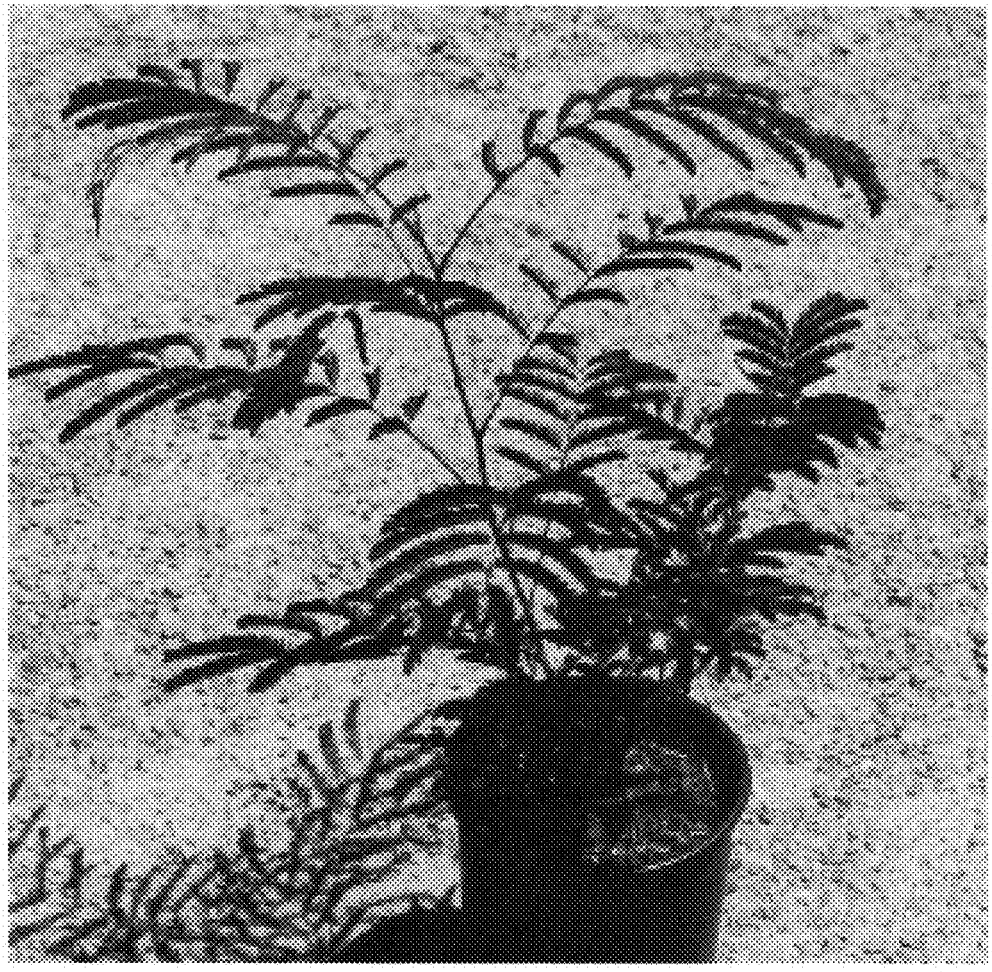

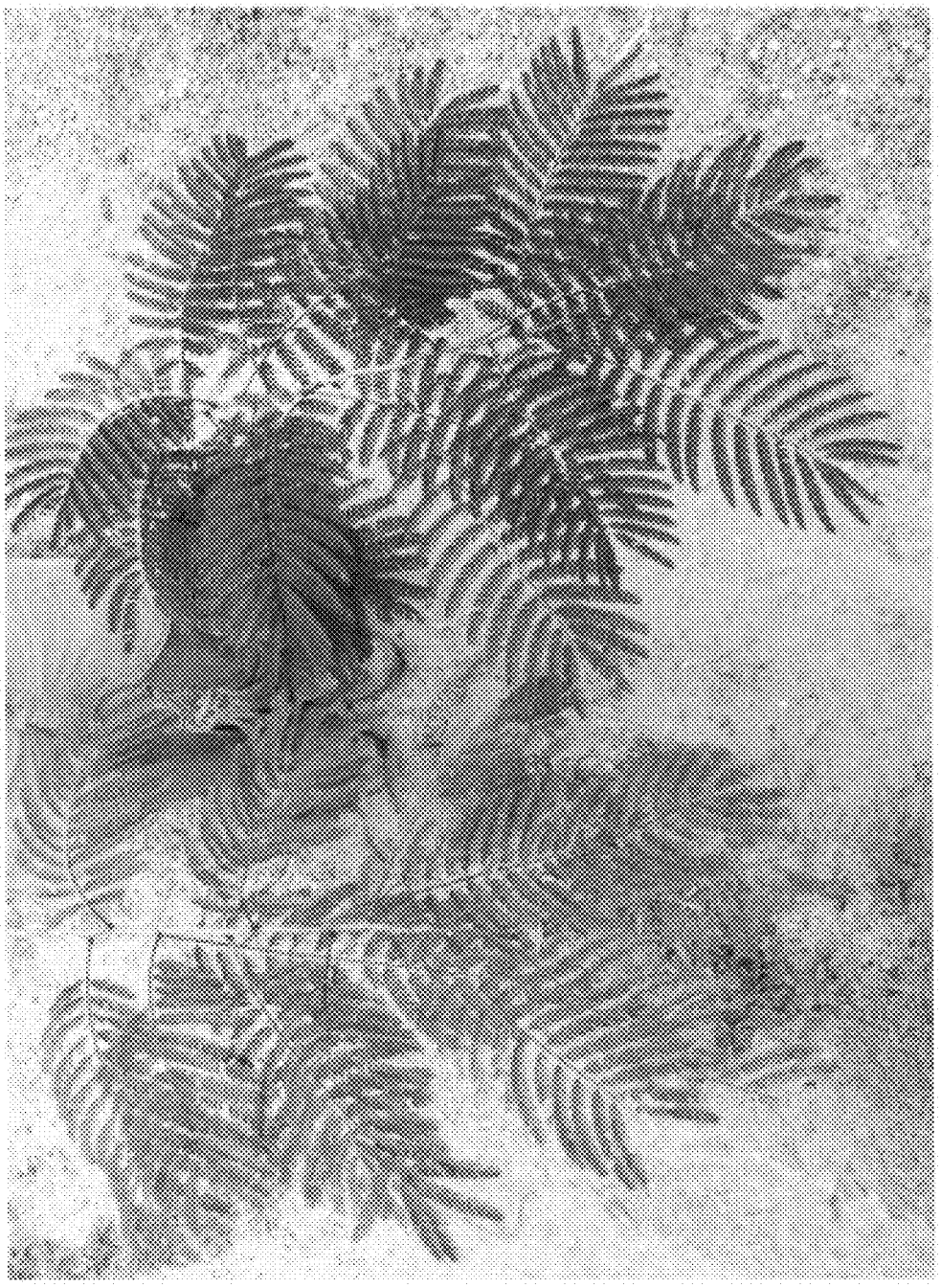

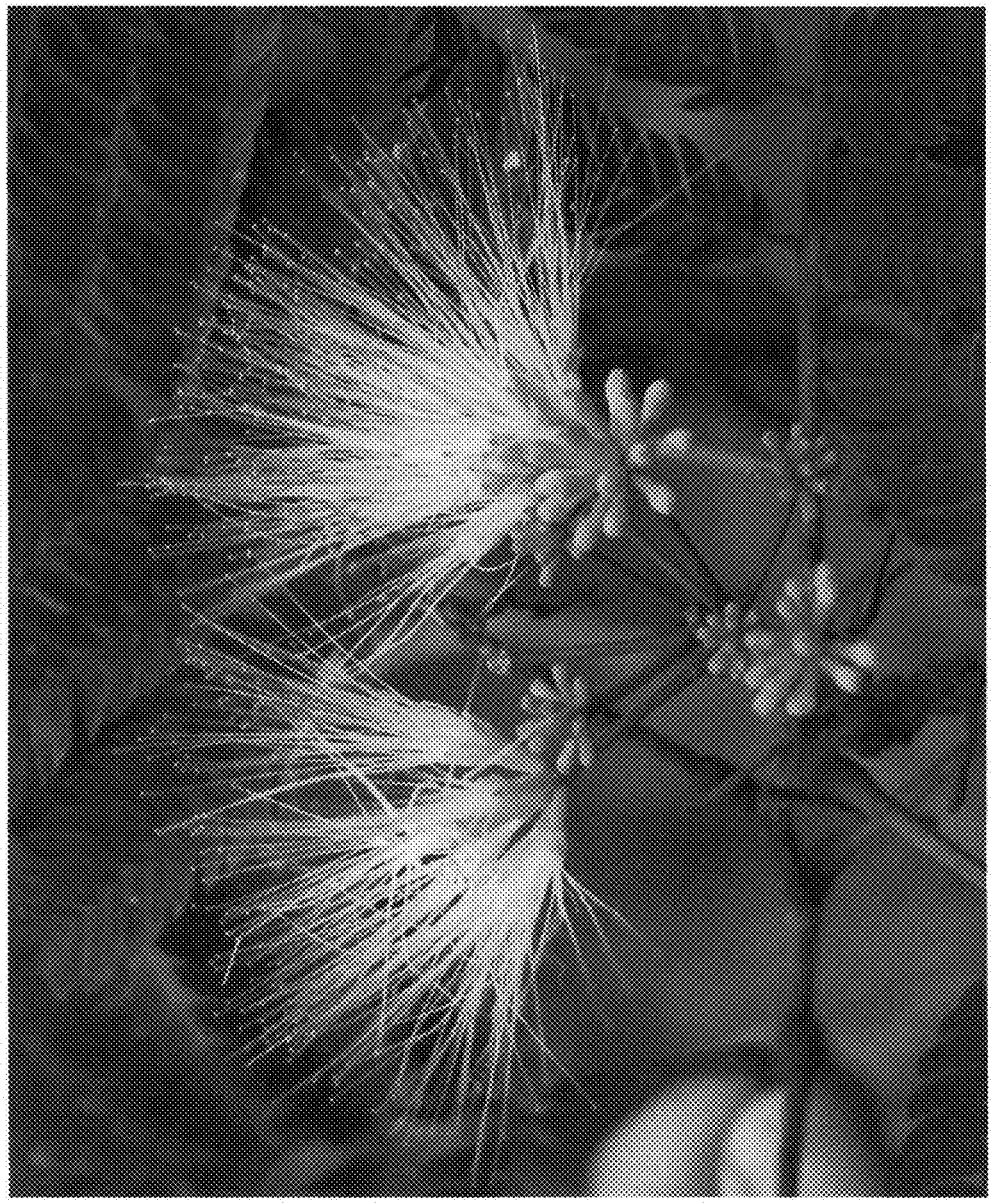

* * * * *